United States Patent [19]

Gilbert et al.

[11] Patent Number: 4,565,785

[45] Date of Patent: Jan. 21, 1986

[54] RECOMBINANT DNA MOLECULE

[75] Inventors: Walter Gilbert; Stephanie A. Broome, both of Cambridge; Lydia J. Villa-Komaroff, Boston; Argiris A. Efstratiadis, Cambridge, all of Mass.

[73] Assignee: The President and Fellows of Harvard College, Cambridge, Mass.

[21] Appl. No.: 519,303

[22] Filed: Aug. 1, 1983

Related U.S. Application Data

[62] Division of Ser. No. 913,533, Jun. 8, 1978, Pat. No. 4,411,994.

[51] Int. Cl.$^4$ .................. C12N 1/00; C12N 15/00; C12N 9/86; C07H 15/12
[52] U.S. Cl. .................. 435/317; 435/172.3; 435/231; 935/48; 536/27
[58] Field of Search .................. 435/172.3, 317, 231; 536/27; 935/10, 14, 47, 48

[56] References Cited

FOREIGN PATENT DOCUMENTS

| | | |
|---|---|---|
| 0001929 | 11/1978 | European Pat. Off. . |
| 0001930 | 11/1978 | European Pat. Off. . |
| 0001931 | 11/1978 | European Pat. Off. . |
| 1521032 | 8/1974 | United Kingdom . |
| 1516458 | 9/1976 | United Kingdom . |
| 2031434A | 8/1979 | United Kingdom . |
| 2033905A | 8/1979 | United Kingdom . |

OTHER PUBLICATIONS

Silhavz et al., PNAS, vol. 74, pp. 5411–5415, Dec. 1977.
Itakura et al., Science, vol. 198, pp. 1056–1063, Dec. 9, 1977.
Aiyappa et al., *J. Bacteriol.* 129, 191 (1977), "Penicillinase-Releasing Protease of *Bacillus licheniformis*: Purification and General Properties".
Alton et al., Gene 4, 241 (1978), "Transcription And Translation in *E. coli* Of Hybrid Plasmids Containing The Catabolic Dehydroquinase Gene From *Neurospora crassa*.
Backman et al., *Proc. Natl. Acad. Sci. USA* 73, 4174 (1976), "Construction of plasmids carrying the cI gene of bacteriophage λ".
Benson and Silhavy, Cell 32, 1325 (1983), "Information within the Mature Lamβ Protein Necessary for Localization to the Outer Membrane of E coli K12".
Blobel and Dobberstein, *J. Cell. Biol.* 67, 835 (1975), "Presence of Proteolytically Processed and Unprocessed Nascent Immunoglobilin Light Chains in Membrane-Bound Ribosomes of Murine Myeloma".
Boime et al., *Biochem. Biophys. Res. Comm.* 62, 103 (1975), "The Translation of a Human Placental Lactogen mRNA Fraction in Heterologous Cell-Free Systems: The Synthesis of a Possible Precursor."
Chang et al., *Proc. Natl. Acad. Sci. USA* 75, 361 (Jan., 1978)."Detection of Prokaryotic Signal Peptidase in an *Escherichia coli* Membrane Fraction: Endoproteolytic Cleavage of Nascent f1 pre-coat Protein".
Cohn et al., *Proc. Natl. Acad. Sci. USA* 69, 1521 (1972), "Calcemic Fraction-A: Biosynthetic Peptide Precursor of Parathyroid Hormone".
Devillers-Thiery et al., *Proc. Natl. Acad. Sci. USA* 72, 5016 (1975), "Homology in amino-terminal sequence of Precursors to Pancreatic Secretory Proteins".
Emr et al., *Proc. Natl. Acad. Sci. USA* 75, 5802 (Dec., 1978) ("*Emr et al. I*"), Mutations Altering the Cellular Localization of the Phage λ Receptor, an *Escherichia coli* outer Membrane protein".
Emr et al., *J. Cell Biology* 86, 701 (1980) ("*Emr et al. II*"), A Mechanism of Protein Localization: The Signal Hypothesis and Bacteria.

(List continued on next page.)

*Primary Examiner*—Alvin E. Tanenholtz
*Attorney, Agent, or Firm*—James F. Haley, Jr.

[57] ABSTRACT

A plasmid or phage gene for a periplasmic or extracellular bacterial protein is cleaved, a double-stranded DNA sequence coding for a selected protein or portion thereof from a eukaryotic cell such as insulin is inserted in that cleaved gene by recombinant DNA techniques and used to transform a bacterium, and the excreted selected protein is collected.

4 Claims, 3 Drawing Figures

OTHER PUBLICATIONS

Fraser and Bruce, *Proc. Natl. Acad. Sci. USA* 75, 5936 (Dec., 1978), "Chicken Ovalbumin is synthesized and secreted by *Escherichia coli*".

Goebel and Hedgpeth, *J. Bacteriol.* 151, 1290 (1982), "Cloning and Functional Characterization of the Plasmid-Encoded Hemolysin Determinant of *Escherichia coli*".

Green et al., *Proc. Natl. Acad. Sci. USA* 72, 224 (1975), "Cell-Free Translation of Immunoglobulin Messenger RNA from MOPC-315 Plasmacytoma and MOPC-315 NR, a Variant Synthesizing Only Light Chain".

Hakkaart et al., *Mol. gen Genet.* 183, 318 (1981), "Protein H Encoded by Plasmic Clo DF13 Involved in Lysis of the Bacterial Host I. Localisation of the Gene and Identification and Subcellular Localisation of the Gene H. Product".

Halegoua et al., *J. Mol. Chem.* 252 2324 (1977), "A New Form of Structural Lipoprotein of Outer Membrane of *Escherichia coli*".

Hall et al., *J. Mol. Biol.* 156, 93 (1982); "Sequence Information within the lam$\beta$ Gene is Required for Proper Routing of the Bacteriophage $\lambda$ Receptor Protein to the Outer Membrane of *Escherichia coli* K-12".

Heidecker and Muller-Hill, *Mol. gen. Genet.* 155, 301 (1977), "Synthetic Multifunctional Proteins. Isolation of Covalently Linked Tryptophan Synthetase $\alpha$-Subunit-*lac*-Repressor-$\beta$-Galactosidase Chimeras".

Hirashima et al., *Proc. Natl. Acad. Sci. USA* 71, 4149 (1974), "Cell-free Synthesis of a Specific Lipoprotein of the *Escherichia coli* Outer Membrane Directed by Purified Messenger RNA".

H. Inouye and Beckwith, *Proc. Natl. Acad. Sci. USA* 74, 1440 (1977), "Synthesis and Processing of an *Escherichia coli* Alkaline phosphatase precursor in vitro".

H. Inouye et al., *J. Mol. Biol.* 110, 75 (1977), "Alkaline Phosphatase Synthesis in a Cell-free System Using DNA and RNA Templates".

M. Inouye and Guthrie, *Proc. Natl. Acad. Sci. USA* 64, 957 (1969), "A Mutation Which Changes A Membrane Protein of E. Coli".

Itakura et al., *Science* 198, 1056-63 (Dec., 1977), "Expression in *Escherichia coli* of a Chemically Synthesized Gene for the Hormone Somatostatin".

Jakes and Zinder, *J. Bacteriol.* 157, 582 (1984), "Plasmid ColE3 Specifies a Lysis Protein".

Kadonaga et al., *J. Biol. Chem.* 259, 2149 (1984), "The Role of the $\beta$-Lactamase Signal Sequence in the Secretion of Proteins by *Escherichia coli*".

Kemper et al., *Proc. Natl. Acad. Sci. USA* 71, 3731 (1974), "Pre-proparathyroid Hormone: A Direct Translation Product of Parathyroid Messenger RNA".

May and Elliott, *Biochim. Biophys. Acta* 157, 607 (1968), "Characteristics Of Extracellular Protease Formation by *Bacillus Subtilis* and Its Control By Amino Acid Repression".

Milstein et al., *Nature New Biology* 239, 117 (1972), "A possible Precursor of Immunoglobulin Light Chains".

Nielsen and Lampen, *ASM News* 49, 318 (1983), "Engineering for Bacterial Secretion".

Palva et al., *Proc. Natl. Acad. Sci. USA* 79, 5582 (1982), "Secretion of *Escherichia coli*$\beta$-lactamase from *Bacillus subtilis* by the aid $\alpha$-amylase signal sequence.

Pugsly and Schwartz, *Mol. gen. Genet.* 190, 366 (1983), "A Genetic Approach to the Study of Mitomycin-Induced Lysis of *Escherichia coli* K-12 Strains which Produce Colicin E2".

Sabik et al., *J. Bacteriol.* 153, 1479 (1983), "*cea-kil* Operon of the ColEl Plasmid".

Schechter, *Proc. Natl. Acad. Sci. USA* 70, 2256 (1973), "Biologically and Chemically Pure mRNA Coding for a Mouse Immunoglobulin L-Chain Prepared with the Aid of Antibodies and Immobilized Oligothymidine".

Scheller et al., *Science* 196, 177-80 (Apr., 1977), "Chemical Synthesis of Restriction Enzyme Recognition Sites Useful for Cloning".

Seeburg et al., *Nature* 276, 795 (Dec., 1978), "Synthesis of growth hormone by bacteria".

Sekizawa et al., *Biochem. Biophys. Res. Comm.* 77, 1126 (1977), "Precursors of Major Outer Membrane Proteins of *Escherichia coli*".

Silhavy et al., *Proc. Natl. Acad. Sci. USA* 73, 3423 (1976) ("Silhavy et al. I"), Conversion of $\beta$-galactosidase to a Membrane-bound State by Gene Fusion.

Silhavy et al., *Proc. Natl. Acad. Sci. USA* 74, 5411 (1977) (*Silhavy et al. II*") Use of Gene Fusions to Study Outer Membrane Protein Localization in *Escherichia coli*.

Suchanek et al., *Eur. J. Biochem.* 60, 309 (1975), "Translation of Honeybee Promelittin Messenger RNA Formation of a Larger Product in a Mammalian Cell-Free System".

Sussman et al., *Proc. Natl. Acad. Sci. USA* 73, 29 (1976), "PreGrowth Hormone: Product of the Translation in vitro of Messenger RNA Coding for Growth Hormone".

Sutcliffe, *Proc. Natl. Acad. Sci. USA* 75, 3737 (Aug., 1978), "Nucleotide Sequence of the Ampicillin Resistance Gene of *Escherichia coli* Plasmid pBR322".

Szczesna and Boime, *Proc. Natl. Acad. Sci. USA* 73, 1179 (1976), "mRNA-Dependent Synthesis of Authentic Precursor to Human Placental Loctogen:Conversion to its Mature Hormone Form in Ascites Cell-Free Extracts".

Takeishi et al., *J. Biol. Chem.* 251, 6259 (1976), "Isolation and Identification of the Messenger Ribonucleic Acid for a Structural Lipoprotein of the *Escherichia coli* Outer Membrane".

Talmadge et al., *Proc. Natl. Acad. Sci. USA* 77, 3988 (1980) ("*Talmadge et al. I*"), Bacteria Mature Preproinsulin to Proinsulin.

Talmadge et al., *Nature* 294, 176 (1981) ("Talmadge et al. II"), An 'internal' Signal Sequence Directs Secretion and Processing of Proinsulin in Bacteria".

Ullrich et al., *Science* 196, 1313 (1977), "Rat Insulin Genes:Construction of plasmids Containing the Coding Sequences".

Villa-Komaroff et al., *Proc. Natl. Acad. Sci. USA* 75, 3727-31 (Aug., 1978), "A Bacterial Clone Synthesizing Proinsulin".

Yamamoto and Lampen, *The J. of Biological Chemistry*, vol. 250, 3212 (1975) ("*Yamamoto and Lampen I*"), Membrane Penicillinase of *Bacillus lichenformis* 749/C, a Phospholipoprotein.

Yamamoto and Lampen, *Proc. Natl. Acad. Sci. USA* 73, 1457 (1976) ("Yamamoto and Lampen II"), Membrane Penicillinase of *Bacillus licheniformis* 749/C: Sequence and Possible Repeated Tetrapeptide Structure of the Phospholipopeptide Region.

Yip et al., *Proc. Natl. Acad. Sci. USA* 72, 4777 (1975), "Translation of Messenger Ribonucleic Acid from Isolated Pancreatic Islets and Human Insulinomonas".

FIG. 1

FIG. 2

```
                                    280                             286
            AsnArgGlnIleAlaGluAlaGlyIleGlyAlaSerLeuIleLysHisTrp
            AATAGACAGATCGCTGAGAGATAGGTGCCTCACTGATTAAGCATTGGTAACTGTCAGACCAAGTTTACTCATATACTTTAGA
                                1040                1060                1080                1100
            TTATCTGTCTAGGGACTCTATCCACGGAGTGACTAATTCGTAACCATTGACAGTCTGGTTCAAATGAGTATATGAAATCT
```

FIG. 3

RECOMBINANT DNA MOLECULE

This is a division, of application Ser. No. 913,533, filed June 8, 1978, now U.S. Pat. No. 4,411,994.

This invention described herein was made in the course of work under a grant or award from the Department of Health, Education and Welfare.

This invention relates to a process for producing specific proteins in bacteria and having them excreted from the bacterial cell and pertains more specifically to inserting the DNA representing the desired non-bacterial protein or part of a protein by recombinant techniques into the plasmid or phage gene for either a periplasmic or an extracellular protein, hereinafter called a "carrier protein", transforming a bacterial host with the recombined gene, and culturing the transformed host to excrete the protein. The protein thus produced can be collected by conventional procedures from the culture medium or from the periplasmic space depending upon the choice of carrier protein gene.

It has previously been proposed to insert DNA representing a specific protein into the gene for an intracellular protein. Itakura et al., Science, Vol. 198,1056 (1977). However, proteins made in this way are mixed with other intracellular proteins and are subject to degradation by enzymes within the cell so that there is a problem in obtaining the desired protein product in purified form.

The process of the present invention, by employing a gene for a carrier protein which has a leader sequence of hydrophobic amino acids at its amino terminus and which is normally excreted through the membrane of the cell within which it is made, with cleavage of the hydrophobic leader sequence during excretion, provides a means for producing a selected protein which can be recovered either from the periplasmic space or from the medium in which the bacterium is grown, depending upon the choice of carrier protein, thus avoiding contamination from the other proteins within the bacterium as well as achieving greater stability by avoiding the enzymes within the bacterial cell which will degrade foreign proteins.

Among the bacterial genes for carrier proteins which can be employed in the present invention are the genes for antibiotic resistance, such as the gene for penicillin resistance or penicillinase, the gene for chloramphenicol resistance, or the gene for tetracycline resistance, as well as the gene for alkaline phosphatase and the gene for bacterial ribonuclease.

Genes or DNA fragments which code for the desired proteins or portions thereof can be inserted in the bacterial carrier protein gene in the process of the present invention. These proteins include a variety of non-bacterial proteins such as eukaryotic cell proteins and viral proteins; of particular importance are eukaryotic cell proteins such as insulin, human growth hormone, interferon and other pharmacologically active proteins, these are synthesized by their respective genes as pre-proteins or precursor proteins having at their amino terminus a series of hydrophobic amino acids. This hydrophobic leader sequence is not identical to that for the bacterial proteins which are excreted through the bacterial membrane. Therefore the fact that pre-insulin or other pre-proteins of higher cells contain a hydrophobic sequence is in itself no basis for expecting that such a pre-protein could be matured in the bacterial cell even if it could be synthesized within the cell. Moreover, the process of the present invention, in addition to providing for the synthesis within and excretion from bacterial cells of matured proteins of eukaryotic cells, which are of known utility, also makes possible the synthesis in and excretion from bacterial cells of other extracellular products of commercial interest these include other fused proteins and fused proteins consisting of carrier proteins, as defined above which carry specific determinants, for example, viral antigens such as coat proteins or other antigenic proteins of viruses these latter fused proteins are useful in the manufacture of vaccines, being capable because of their antigenic character of inducing generation of an immune response specific to the viruses. Such vaccines will be unusually safe because they will not contain any live or inactivated virus material. Furthermore, it will by this process be possible to construct vaccines for viruses which cannot be grown in culture.

Figure 1:
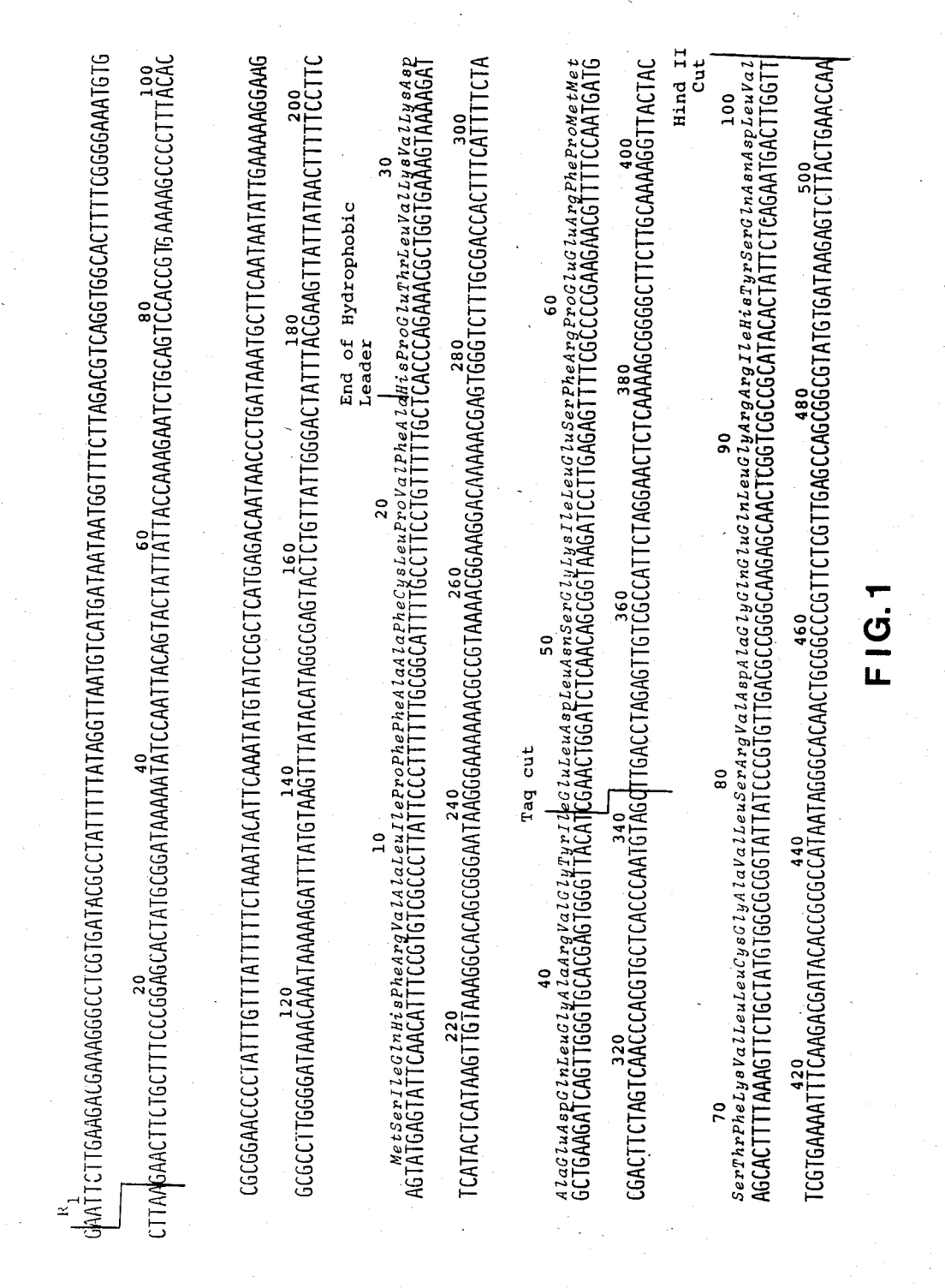
Figure 2:
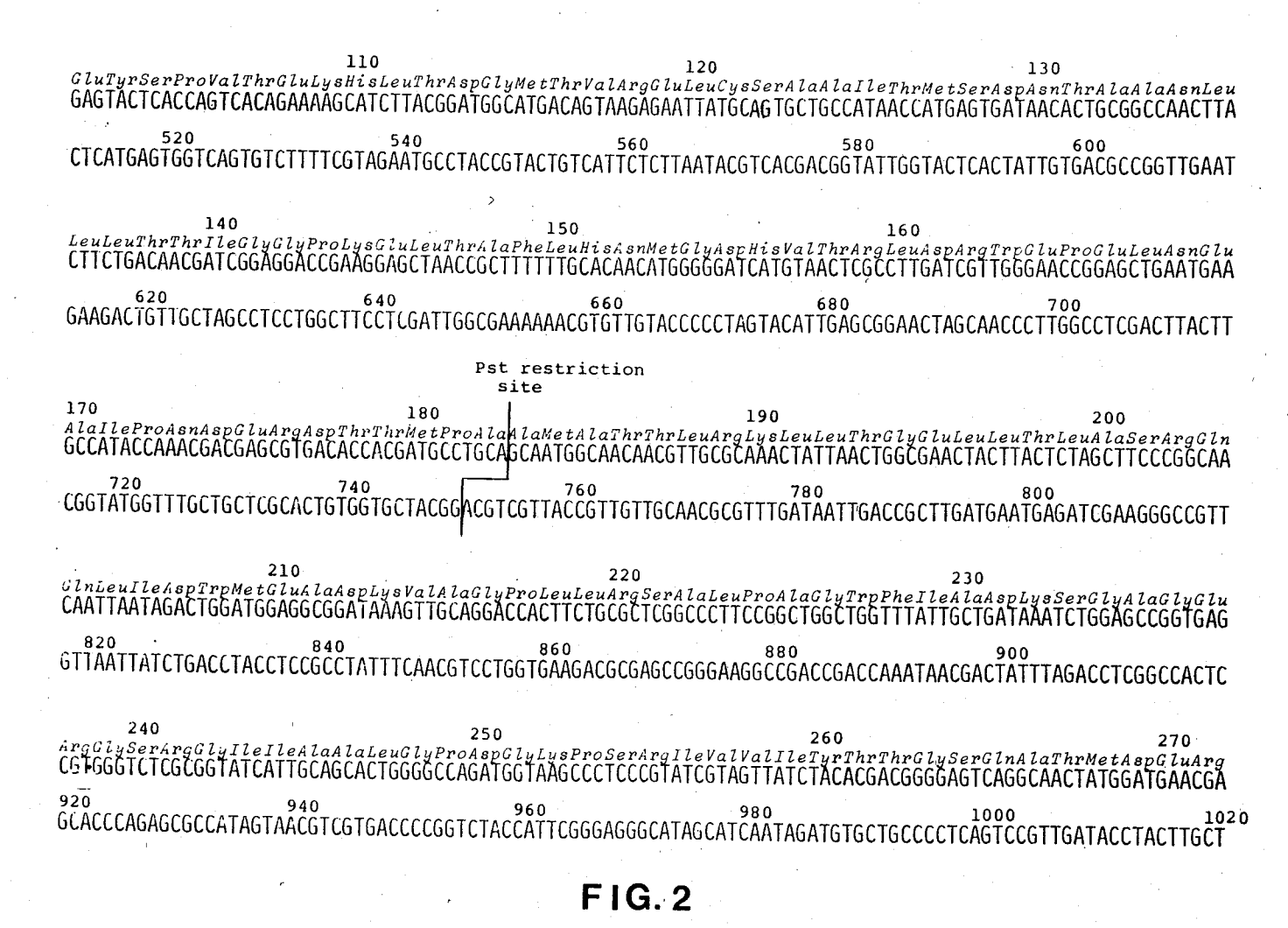

FIGS. 1, 2 and 3 of the drawing show the complete base sequence for the E. coli penicillinase gene carried on the plasmid pBR322 along with the corresponding amino acid sequence of the protein for which it codes.

The following specific example is intended to illustrate more fully the nature of the present invention without acting as a limitation upon its scope.

EXAMPLE

There was employed as the carrier protein E. coli penicillinase, the gene for which is carried on the small plasmid pBR322. A restriction enzyme map of this gene is as shown in the drawing. This plasmid vector has been described by Bolivar et al., Gene, Vol. 2, page 95 (1977). There was employed as the host bacterium E. coli 1776, see Curtiss et al. in recombinant Molecules, Impact on Science and Society, Proceedings of the Tenth Miles International Symposium, eds. Beers & Bassett, pages 45–56 (1977). The host-vector combination is a certified EK2 system certified by the NIH, July 7, 1977.

The plasmid carries a Pst [(Providencia Stuartii endonucleuse] restriction site of the penicillinase gene corresponding to the position of amino acids 181 and 182, as shown in the drawing. Double stranded cDNA was synthesized from RNA containing preproinsulin on RNA(PPI-mRNA) isolated from an X-ray induced, transplantable rat B-cell tumor (Chick et al., P.N.A.S. 74, 628–632 (1977)). Batches of 20 g each of frozen tumor slices were ground with sterile sand with mortar and pestle and the cytoplasmic RNA purified from a post-nuclear supernatant by $Mg^{2+}$ precipitation (Palmiter, R. Biochemistry 13, 3606 (1974)) followed by extraction with phenol and chloroform. This RNA was further purified by oligo-dT-cellulose chromatography (Aviv and Leder, P.N.A.S. 69, 1408 (1972)) and used directly as template for double-stranded cDNA synthesis, as described (Efstratiadis et al., Cell 7, 279 (1976)), except that a specific P $(dT)_8$ dG-dC primer (Collaborative Research) was utilized for reverse transcription. The concentrations of RNA and primer were 7 mg/μl and 1 mg/μl, respectively. All four $\alpha$-$^{32}$P-dNTPs were at 1.25 mM (final specific activity 0.85 Ci/m mole). The reverse transcript was 2% of the input RNA, and 25% of it was finally recovered in the double-stranded DNA product.

The double-stranded cDNA was inserted into the Pst site of plasmid pBR322 by the following procedure: pBR322 DNA (5.0 μg) was linearized with Pst and approximately 15 dG residues were added per 3' end by terminal transferase at 15° C. in the presence of 1 mM $Co^{2+}$ (Raychoudhury et al., Nucl. Acids Res., 3, 101 (1976)) and 100 μg/ml autoclaved gelatin. The same procedure was used to add dC residues to 2.0 μg of double-stranded cDNA. The reaction mixtures were extracted with phenol, and ethanol precipitated. The dC tailed double-stranded cDNA was electrophoresed in a 6% polyacrylamide gel under native conditions. Following autoradiography, molecules in the size range of 300 to 600 base pairs (0.5 μg) were eluted from the gel (Efstratiadis and Kafatos in Methods in Molecular Biology, 8, 1–124 (1976)). The eluted double-stranded cDNA was concentrated by ethanol precipitation, redissolved in 10 mM Tris pH 8, mixed with 5 μg dG tailed pBR322 and dialyzed versus 0.1 M NaCl, 10 mM EDTA, 10 mM Tris pH 8. The mixture (4 ml) was then heated at 56° for 2 minutes, and annealing was performed at 42° for 2 hours. The hybrid DNA was used to transform *E. coli* X 1776. The use of oligo dC-dG joins regenerates the Pst cuts so that the insert may be later excised.

Transformation of *E. coli* X1776, an EK-2 host with pBR322, an EK-2 vector, was performed in a biological safety cabinet in a P3 physical containment facility in compliance with N.I.H. guidelines for recombinant DNA research published in the *Federal Register*, July 7, 1976.

X1776 was transformed by a transfection procedure (Enea et al., J. Mol. Biol., 96, 495 (1975) slightly modified as follows: X1776 was grown in L Broth [10 gms tryptone, 5 g yeast extract, 5 gm NaCL (Difco)] supplemented with 10 μg/ml diaminopimelic acid and 40 μg/ml thymidine (Sigma) to $A_{590}$ of 0.5. A 200 ml portion of cells were sedimented at 3000 rpm and resuspended by swirling in 1/10 volume of cold buffer containing 70 mM $MnCl_2$, 40 mM NaAc pH 5.6, 30 mM $CaCl_2$ and kept on ice for 20 minutes. The cells were repelleted and resuspended in 1/30 of the original volume in the same buffer. The annealed DNA (2 ml) was added to the cells. Aliquots of this mixture (0.3 ml) were placed in sterile tubes and incubated on ice 60 minutes. The cells were then placed at 37° for 2 minutes. Broth was added to each tube (0.7 ml) and the tubes incubated at 37° for 15 minutes. A 200 μl portion of the cells was spread on sterile nitrocellulose filters (Millipore) overlaying agar plates containing 15 μg/ml tetracycline. (The filters were boiled to remove detergents before use.)The plates were incubated at 37° for 48 hours. Replicas of the filters were made. The nitrocellulose filters containing the transformants were removed from the agar and placed on a layer of sterile Whatman filter paper. A new sterile filter was placed on top of the filter containing the colonies and pressure was applied with a sterile velvet cloth and a duplicate block. A sterile needle was used to key the filters. The second filter was placed on a new agar plate and incubated at 37° for 48 hr. The colonies on the first filter were screened by the Grunstein-Hogness (P.N.A.S. 72, 3961 (1975)) technique, using as probe an 80-nucleotide long fragment produced by Hae III digestion of high specific activity cDNA copied from the rat oligo-dT bound RNA. Positive colonies were rescreened by the Hart method (Paterson, Roberts and Kuff. P.N.A.S. 74, 4370 (1977)) as follows: Plasmid DNA (about 3 μg) was digested with Pst, ethanol precipitated, and dissolved directly into 20 μl dionized formamide. After heating for one minute at 95° each sample was placed on ice. After the addition of 1.5 μg oligo (dT)-cellulose bound RNA, PIPES pH 6.4 to 10 mM and NaCl to 0.4 M, the mixtures were incubated for 2 hr at 50°. They were then diluted by the addition of 75 μl $H_2O$ and ethanol precipitated in the presence of 10 μg wheat-germ tRNA, washed with 70% ethanol, dissolved in $H_2O$ and added to a wheat-germ cell-free translation mixture (Roberts and Paterson, P.N.A.S. 70, 2330 (1973)). After three hours at 23° C., duplicate 2 μl aliquots were removed for trichloroacetic acid precipitation; the remainder of the reaction mixture was treated with ribonuclease, diluted with immunoassay buffer, and analyzed for the syntheses of immunoreactive preproinsulin by means of a double antibody immunoprecipitation (Lomedico and Saunders, Nucl. Acids Res. 3, 381 (1976)). The washed immunoprecipitates were dissolved in 1 ml of NCS (Amersham) and counted in 10 μl of Omnifluor (New England Nuclear) by liquid scintillation.

One colony was identified by the HART Screening. The Pst excisable insert was sequenced by the method of Maxam and Gilbert (P.N.A.S. 74, 560 (1977)) to show that it corresponded to the sequence of rat preproinsulin I. This insert, labeled by nick translation with DNA polymerase I was used to screen 2000 transformants with the Grunstein-Hogness assay. There were identified 48 clones hybridizing to the rat preproinsulin cDNA Probe.

These 48 clones of transformed *E. Coli* 1776 were screened using an in situ radioimmunoassay technique to determine whether the clones were producing insulin antigens and whether they were producing fused polypeptide chains, one end of which being insulin antigen and the other end penicillinase (the bacterial carrier protein) antigen. Presence of the fused polypeptide chains would indicate that the clones contained genes which were the products of the fusion of the bacterial gene for penicillinase with the eukaryotic cell gene for insulin. Such fused polypeptide chains were in fact found, using the technique to be described below. The technique takes advantage of the fact that the fused proteins being searched for contain two antigenic ends, each of which will bind to its respective specific antibody. A specific antibody was laid down on a plastic disk, the antigenic protein from lysed bacterial cells placed in contact with this disk, then the disk was rinsed and exposed to radioactive antibodies. A protein molecule will bind to the antibody fixed to the plastic with one antigenic determinants and will bind in turn a radioactive antibody with a second determinant. If anti-penicillinase is on the disk and anti-insulin is labeled, after the "sandwich" is washed, the only points of radioactivity remaining will mark the presence of fused proteins. In more detail, the method was as follows:

Each 8.25 cm diameter disk of clear polyvinyl (PV) 8 mm thick (Dora May Co., New York) was flattened between sheets of smooth paper. In a glass petri disk, each disk was then placed upon the surface of a liquid containing 10 ml of 0.2 M$NaHCO_3$, at pH 9.2, containing 60 μg/ml IgG. After 2 minutes or longer at room temperature, the disk was removed and washed twice with 10 ml of cold wash buffer (WB), which consisted of phosphate-buffered saline, 0.5% normal guinea pig serum, 0.1% bovine serum albumin and 0.3 mg/ml streptomycin sulfate. Each disk was used immediately after washing.

Antigens were released from bacterial cells by transferring colonies onto 1.5% agarose containing 0.5 mg lysozyme/ml, 30 mM Tris pH 8, and 10 mM EDTA. The IgG-coated surface of a PV disk was placed faced down on the agarose and bacterial colonies and left for 60 minutes at 4°. Each disk was then removed and washed 3 times with 10 ml of cold WB. This step completed the immunoadsorption of antigen onto the solid-phase antibody layer.

Reaction of the $^{125}$I-labeled antibodies with the antigen now adhering to the disks was done by setting 1.5 ml WB containing $5\times10^6$ cpm ($\delta$ emission) 125I-IgG onto the center of an 8.25 cm diameter flat disk of ordinary nylon mesh which had been placed in the bottom of a petri dish. The mesh served as a spacer. A disk treated as in the earlier steps then was placed face down on the mesh and solution and incubated overnight at 4°. Each disk was then washed twice with 10 ml cold WB and twice with water, and allowed to dry at room temperature. At this point, fused proteins had bound to both the ordinary and radioactively labeled layers of IgG. These proteins were then detected with conventional autoradiography technique using Kodak No. Screen Film or Kodak X-OMAT R film and a DuPont Cronex Lighting plus intensifying screen as described for example by Laskey et al., FEBS Lett., Vol. 82, pages 314–316 (1977). Both anti-insulin and anti-penicillinase IgG fractions were required for the procedure above. The anti-insulin antiserum was a commercially available product obtained from guinea pigs. The rabbit anti-penicillinase anti-serum was produced by injecting (1 mg pure) penicillinase (in complete Freund's adjuvant (Difco)) into New Zealand white rabbits. (Booster injections were administered in incomplete Freund's adjuvant (Difco)) 2 and 3 weeks after the initial injection, and the rabbits were bled 1 week later.

The IgG fractions were prepared from each immune serum by ammonium sulfate precipitation followed by DEAE-cellulose (Whatman, DE-52) chromatography in 0.025 M potassium phosphate, pH 7.3, 1% glycerol. Fractions containing the bulk of the flow-through material were pooled, and protein was precipitated by adding ammonium sulfate to 40% saturation. The resulting pellet was resuspended in $\frac{1}{3}$ the original serum volume of 0.025 M potassium phosphate, pH 7.3, 0.1 M NaCl, 1% glycerol, and dialyzed against the same buffer. After dialysis, any residual precipitate was removed by centrifugation. IgG fractions were stored in aliquots at $-70°$.

Each IgG fraction was radioiodinated by the usual method of Hunter and Greenwood, Biochem. J., Vol. 91, pages 43–46 (1964). The 25 $\mu$l reaction mixture contained 0.5 M potassium phosphate, pH 7.5, 2 mCi carrier-free Na$^{125}$I, 150 $\mu$g IgG and 2 $\mu$g chloramine T. After 3 minutes at room temperature, 8 $\mu$g of sodium metabisulfite in 25 $\mu$l PBS was added, followed by 200 $\mu$l PBS containing 2% normal guinea pig serum. The $^{125}$I-labeled IgG was purified by chromatography on a Sephadex G-50 column equilibrated with PBS containing 2% normal guinea pig serum. The $^{125}$I-IgG elution fraction was diluted to 5 ml with PBS containing 10% normal guinea pig serum, filtered through a sterile Millipore VC filter (0.1 $\mu$m pore size), divided into aliquots and stored at $-70°$. The specific activities were $1.5\times10^7$ cpm/$\mu$g.

This screening detected one clone of X 1776 that synthesized and secreted a fused protein showing both penicillinase and insulin antigenic determinant. This protein, recovered from the periplasm, mimics insulin in radioimmunoassays. DNA sequencing shows that this protein is a fusion between penicillinase and proinsulin, the two proteins being connected by 6 glycines between amino acid 182 of penicillinase (Alanine) and amino acid 4, glutamine, of proinsulin. Thus a higher cell hormone has been synthesized in bacteria in an antigenically active form.

It will be appreciated that the DNA sequence for the desired eukaryotic cell protein can be inserted into a Hind II cut corresponding to the position between amino acids 101 and 102 of the protein for which this pBR322 plasmid codes, or into the Taq cut at the position corresponding to amino acid 45. In all cases, if the eukaryotic cell DNA is arranged in phase, by the random addition of tails or by other procedures, it will be expressed as a fused part of the carrier protein; and the protein excreted from the cell. furthermore, the sequence of the penicillinase gene, as it exists in this plasmid, or in others, can be modified either by mutation, or by direct recombinant DNA techniques such as the insertion of DNA fragments at specific points within the gene, in such a way as to insert new restriction cuts that are convenient for splicing. For example, the R1 cut on the plasmid pBR322 can be removed by mutation, and an R1 sequence inserted by ligation into the penicillinase gene. Although this might inactivate the gene, it would not interfere with the use of this region of DNA to synthesize a carrier protein.

The segment of the penicillinase gene DNA between the code for amino acid 23 at the end of the hydrophobic leader and the code for amino acid 45 at the Taq cut for example, can be removed by nibbling back the DNA by a mixture of appropriate enzymes. One such mixture is the lambda exonuclease which will chew back the DNA strand from the 5' end, together with the enzyme S1, which will remove the single stranded overhang. Another such mixture is T$_4$ DNA polymerase which will chew back the 3' end of one DNA strand together with S1 which again will remove the single stranded overhang. By controlled digestion the plasmid DNA molecule can be appropriately shortened to the fragment extending from the R1 cut to the point coding for amino acid 23 or to other points on the hydrophobic leader sequence, and such a fragment can be fused to a similarly generated fragment containing the insulin sequence, chewed back enzymatically to a convenient initial point, presumably, again, the point where the mature insulin molecule begins. These two fragments can be fused together, for example, by butt end ligation by the T$_4$ DNA ligase, and that fusion inserted into the plasmid. That fusion produces a degenerate species of the carrier protein, for which the carrier gene codes for only the *E. coli* hydrophobic leader sequence and the eukaryotic cell gene provides the rest of the structural information. Although such constructions can in principle be done exactly, in practice they will probably be done on a random basis, involving the splicing of a variety of gene fragments whose end points are in interesting regions, and examining the medium surrounding clones of bacteria transformed by the fused fragments to detect antigenic activity by an RIA such as the one described above, as evidence of protein synthesis.

The procedure of the present invention is not restricted to the use of the *E. Coli* 1776 or penicillinase gene, but is applicable to bacterial host in general and to the gene for any excreted protein carried on a multicopy plasmic or on a phage. It is not restricted to insulin, but can be used to find the expression of the fused protein of an y DNA fragment of a virus or eukaryotic cell that carries a coding region that codes, when translate in phase, for antigenic determinants in the viral or eukaryotic cell protein. Thus if fragments of animal virus DNA are inserted into the Pst or Hind II site of the penicillinase gene, some recipient bacterium will synthesize a fused protein which will be recognizable by using the RIA technique, employing antibodies specific to the viral antigen. This fused protein in turn can be purified and used to stimulate an antibody response in an animal or person, either for the production of antibodies directed at specific sites on the virus protein, or as vaccination against the viral antigen. The fused protein will provide helper determinants in such a vaccination, to aid the immune response, although, presumably, aggregated states of the fused protein would have to be used in a vaccine. The specific carrier proteins that would be used might be either the bacterial proteins themselves or still further fusions between the bacterial proteins and other convenient sequences to provide useful helper determinants in carrier proteins.

What is claimed is:
1. A recombinant DNA molecule comprising a bacterial gene for an extracellular or periplasmic carrier protein and a non-bacterial gene which codes for a selected protein or polypeptide, said non-bacterial gene having been inserted into said bacterial gene and joined end to end with a portion thereof so as to maintain constant the proper reading frame in both genes.
2. The recombinant DNA molecule of claim 1 wherein said non-bacterial gene has been inserted into said bacterial gene at a restriction endonuclease site therein.
3. The recombinant DNA molecule of claim 2 wherein the restriction endonuclease site is the Pst site.
4. The recombinant DNA molecule of claim 1 wherein the bacterial gene is the gene for *E. coli* penicillinase.

* * * * *